United States Patent
Ashurst

(10) Patent No.: US 9,017,666 B2
(45) Date of Patent: Apr. 28, 2015

(54) BROCCOLI BASED NUTRITIONAL SUPPLEMENTS

(71) Applicant: Jarrow Formulas, Inc., Los Angeles, CA (US)

(72) Inventor: Kean Ashurst, Taylorsville, KY (US)

(73) Assignee: Jarrow Formulas, Inc., Los Angeles, CA (US)

( * ) Notice: Subject to any disclaimer, the term of this patent is extended or adjusted under 35 U.S.C. 154(b) by 0 days.

(21) Appl. No.: 13/910,576

(22) Filed: Jun. 5, 2013

(65) Prior Publication Data

US 2013/0323225 A1    Dec. 5, 2013

Related U.S. Application Data

(60) Provisional application No. 61/655,569, filed on Jun. 5, 2012.

(51) Int. Cl.
*A23L 1/30* (2006.01)

(52) U.S. Cl.
CPC ................................ *A23L 1/3002* (2013.01)

(58) Field of Classification Search
CPC ........... A61K 8/97; A61K 6/31; A61K 36/00; A61K 38/00; A61K 38/46; A61K 38/47; A23L 1/015; A23L 1/0152; A01N 25/00; A01N 25/002; C12N 9/00; C12N 9/14; C12N 9/24

See application file for complete search history.

(56) References Cited

U.S. PATENT DOCUMENTS

| | | | |
|---|---|---|---|
| 5,411,986 A | 5/1995 | Cho et al. | |
| 5,725,895 A | 3/1998 | Fahey et al. | |
| 5,968,505 A | 10/1999 | Fahey et al. | |
| 5,968,567 A | 10/1999 | Fahey et al. | |
| RE36,784 E | 7/2000 | Cho et al. | |
| 6,177,122 B1 | 1/2001 | Fahey et al. | |
| 6,242,018 B1 | 6/2001 | Fahey et al. | |
| 6,521,818 B1 | 2/2003 | Fahey | |
| 7,303,770 B2 | 12/2007 | Fahey et al. | |
| 2007/0009576 A1* | 1/2007 | Stillman | 424/439 |
| 2008/0131578 A1 | 6/2008 | Caudill et al. | |
| 2008/0311192 A1 | 12/2008 | West et al. | |
| 2009/0081138 A1 | 3/2009 | Ashurst | |
| 2012/0213890 A1 | 8/2012 | Sullivan et al. | |

OTHER PUBLICATIONS

Matusheski, N. V. et al. 2006. Epithiospecifier protein from broccoli (Brassica oleracea L. ssp. italica) inhibits formation of the anticancer agent sulforaphane. Journal of Agricultural and Food Chemistry 54:2069-2076. specif., p. 2069-2070.*

Self Nutrition Data. Datasheet [online]. Copyright 2014, Conde Nast [retrieved on May 1, 2014]. Retrieved from the Internet: <URL: http://nutritiondata.self.com/facts/vegetables-and-vegetable-products/2356/2>. p. 2.*

Cramer, J.M. et al. 2011. (First published online Jan. 13, 2011). Sulforaphane absorption and excretion following ingestion of a semi-purified broccoli powder rich in glucoraphanin and broccoli sprouts in healthy men. Nutrition and Cancer 63(2):196-201. specif. pp. 196-197.*

Merriam-Webster Dictionary. Datasheet [online]. Copyright 2014, Merriam-Webster, Inc. [retrieved on Apr. 30, 2014]. Retrieved from the Internet: <URL: http://www.merriam-webster.com/dictionary/rich>. p. 1.*

Cytotoxic and Cancerostatic Activity of Isothiocyanates and Related Components, K. Horakova, et al, Neoplasma 15, 2, 1968, pp. 169-176.

Differential Expression of Myrosinase Gene Families, Marit Lenman, et al., Plant Physiol. (1993) 103: 703-711.

The myrosinase-glucosinolate system, its organisation and biochemistry, Atle M. Bones, et al., Physiologia Plantarum 97: 194-208, 1996.

Degeneration of HeLa-Cells Induced By The Cytotoxic Effect of Isothiocyanates or By The Starvation Cells, K. Horakova, et al, Acta Morphologica Acad. Sci. Hung. 18(3), pp. 193-202, 1970.

Supercritical CO2 Extraction and Processing of Oilseeds, G.R. List, et al, Oil Mill Gazetteer, Dec. 1989, pp. 28-34.

Studies on the Mechanism of Myrosinase, Investigation of the Effect of Glycosyl Acceptors on Enzyme Activity, M. Grazia Botti, et al., The Journal of Biological Chemistry, vol. 270, No. 35, Sep. 1, 1995, pp. 20530-20535.

Physiological Modeling of the Small Intestine in Drug Absorption, K. Sandy Pang, Deparment of Pharmaceutical Sciences, University of Toronto, pp. ASH00335-ASH00364.

Heating decreases epithiospecifier protein activity and increases sulforaphane formation in broccoli, Nathan V. Matusheski, et al., Phytochemistry 65 (2004) 1273-1281.

Effects of metal ions on myrosinase activity and the formation of sulforaphane in broccoli seed, Hao Liang, et al., Journal of Molecular Catalysis B: Enzymatic 43 (2006) 19-22.

Glucosinolates, isothiocyanates and human health, Maria Traka, et al., Phytochem Rev. (2009) 8:269-282.

(Continued)

*Primary Examiner* — John S Brusca
*Assistant Examiner* — Sharon M Papciak
(74) *Attorney, Agent, or Firm* — McCarter & English, LLP

(57) ABSTRACT

A nutritional supplement is provided containing two broccoli based components that are combined and, when ingested, react in the intestines to provide sulforaphane. Processes for producing the broccoli components of the nutritional supplement are also provided. The broccoli components are treated separately using supercritical fluid extraction to remove oils. The temperature and pressure of the supercritical extraction processes are controlled to provide broccoli components having the desired properties for the nutritional supplement.

7 Claims, No Drawings

(56) References Cited

OTHER PUBLICATIONS

Glucosinolates in Cruciferous Plants, Cecil H. Vanetten, et al., pp. 511-520.
Effect of processing on bioactives in vegetables: the case for more research on broccoli, Elizabeth Jeffery, University of Illinois at Urbana.
Absorption/Metabolism of Sulforaphane and Quercetin, and Regulation of Phase II Enzymes, in Human Jejunum in Vivo, Niclas Petri, et al., Drug Metabolism and Disposition, vol. 31, No. 6, pp. 805-813.
Cruciferous Vegetables and Cancer Prevention, Cynthia A. Thomson, et al., Functional Foods & Nutraceuticals in Cancer Prevention, 15, pp. 263-270.
Conversion of Glucosinolates to Isothiocyanates in Humans After Ingestion of Cooked Watercress, Serkadis M. Getahun, et al., Cancer Epidemiology, Biomarkers & Prevention, vol. 8, 447-451, May 1999.
Functional Analysis of Plant Idioblases (Myrosin Cells) and Their Role in Defense, Development and Growth, Birgit Hafeld Borgen, UNIGEN Center of Molecular Biology and Department of Biology, Faculty of Natural Sciences and Technology, Norwegian University of Science and Technology, 2002, Thesis.
Broccoli under Pressure, Optimizing yield and durability of functional components from Broccoli sprouts by extraction with supercritical CO2, K. Ashurst, et al., CSHealth, Nateco.
BroccoRaphanin, Manufacturing Flow, C S Health, Louisville, KY.
Pathway: glucosinolate breakdown, MetaCyc.

* cited by examiner

BROCCOLI BASED NUTRITIONAL SUPPLEMENTS

This application claims priority under 35 U.S.C. §119(e) to U.S. Provisional Application No. 61/655,569 filed on Jun. 5, 2012, the entire contents of which are hereby incorporated by reference.

FIELD OF THE INVENTION

The present invention is directed, in one aspect, to a nutritional supplement containing components that, when ingested, react in the intestines to provide a source of sulforaphane. In another aspect, the present invention is directed to a process for producing the nutritional supplement. In particular, the present invention can provide a broccoli based nutritional supplement preserving the natural broccoli seed matrix.

BACKGROUND

Sulforaphane is believed to provide various health benefits, including potential anti-cancer benefits, as described by Horakova et al., Cytotoxic and Cancerostatic Activity of Isothiocyanates and Related Compounds, Neoplasma, Vol. 15, No. 2 (1968). Sulforaphane is an unstable and reactive product. Accordingly, it would be beneficial to provide a nutritional supplement containing components that, when ingested, react within the intestines to provide a source of sulforaphane. The release of sulforaphane in the intestine allows the sulforaphane to be absorbed by the body. This is believed to be beneficial because sulforaphane facilitates detoxification of xenobiotics and other toxins by the liver. Sulforaphane is also a bi-functional inducer of Phase II enzymes, elevating some Phase II enzymes while down regulating others.

It is generally desirable to produce nutritional supplements using natural products. Glucoraphanin, also known as sulforaphane glucosinolate, is a sulfonated (sulfur-bearing) sugar contained in various crucifers, including broccoli seeds, sprouts and florets. Myrosinase is an enzyme also contained in broccoli seeds, sprouts and florets. Myrosinase hydrolyzes glucoraphanin (a glucosinolate) to release sulforaphane (an isothiocyanate). This reaction is redirected to sulforaphane nitrile by epithiospecifier protein (ESP), which is also present in broccoli seeds, sprouts and florets. ESP can be deactivated by heating the broccoli product to a temperature above 140° F., but care must be taken to avoid higher temperatures, as myrosinase can itself be deactivated at temperatures of about 185° F. and above.

In producing a nutritional supplement using broccoli seeds or sprouts, it is generally desirable to first produce a glucoraphanin rich meal, as it is the glucoraphanin that provides a source of sulforaphane. Higher concentrations of glucoraphanin in the meal can result in release of more sulforaphane from the nutritional supplement. There are various known methods that may be used to produce a glucoraphanin rich meal. For example, it has been known to produce a glucoraphanin rich meal using supercritical fluid extraction (SCFE) to remove the natural oils present in the broccoli. Natural oils can comprise 30% to 50% of the weight of the broccoli seed or sprout. In one process for producing a glucoraphanin rich meal, described in U.S. Patent Publication No. 2009/0081138, broccoli seeds, sprouts or florets are deoiled by SCFE using carbon dioxide. The broccoli material is first ground, milled, chopped or flaked. Flake rolling opens or stretches the cells to allow access of the supercritical $CO_2$ to the cells for extraction of the oils. The broccoli material is then fed into a supercritical $CO_2$ chamber for batch-wise supercritical extraction of the oil to create a glucoraphanin rich meal. Depending upon the temperature, pressure and time used for the SCFE process, up to 98% of the oil in the broccoli material can be extracted.

To avoid unwanted reaction of myrosinase with the glucoraphanin, the myrosinase in the broccoli material is typically deactivated before or during the SCFE process. Prior nutritional supplements then combined the glucoraphanin rich meal with myrosinase obtained separately from broccoli or other sources. Various processes for water extraction of myrosinase from broccoli or other crucifers that contain myrosinase are known. These or other processes have been used in the past to provide myrosinase.

It would be desirable to have a broccoli based nutritional supplement in which myrosinase is provided in its natural form in broccoli. Accordingly, the present invention provides a nutritional supplement, and a process for producing the nutritional supplement, in which a first deoiled broccoli powder which is rich in glucoraphanin is combined with a second broccoli powder containing active myrosinase.

DETAILED DESCRIPTION OF THE INVENTION

In the present invention, two broccoli based materials are each treated and then combined to produce a nutritional supplement. A first material comprising a glucoraphanin rich meal produced from broccoli seeds or sprouts is combined with a second material in which broccoli seeds have been treated to deactivate the ESP while maintaining activity of the myrosinase. The first and second broccoli materials are combined in an acid resistant or enteric coated capsule. When ingested, the first and second broccoli materials are released in the intestines under conditions in which the glucoraphanin in the first material is hydrolyzed by the myrosinase in the second material to release sulforaphane. To further enhance the conversion, ascorbate may be added to the nutritional supplement. Small amounts of ascorbate at the multiple reaction sites on the myrosinase enzyme facilitates the conversion of the glucoraphanin to sulforaphane in the intestine.

The present invention also relates to an improved process for providing a source of myrosinase for a nutritional supplement, and to nutritional supplements containing the myrosinase source. In the process of the present invention, broccoli seed is first prepared for extraction of oils using known techniques, such as for example by flaking and rolling. Flaking and rolling stretches the cells to allow access of the supercritical $CO_2$ to the cells for extraction of the oils.

A first quantity of flake rolled broccoli seed is deoiled by SCFE to remove a large quantity of the oil in the seeds using known techniques, such as those described in U.S. Patent Application No. 2009/0081138. In one embodiment, the broccoli seed is treated using carbon dioxide as the extraction fluid. In the present invention, the SCFE process is conducted at pressures of up to about 600 bar and a temperature of about 185° F. This process produces a seed meal containing 1-2% or less oil.

A second quantity of flake rolled broccoli seed is partially deoiled using SCFE at temperatures sufficient to deactivate the ESP while preserving the myrosinase. Any appropriate fluid may be used in the SCFE process. In one embodiment, supercritical carbon dioxide is used in the SCFE process. Carbon dioxide is preferred because it provides for safe handling and disposal.

The prepared broccoli seed is treated using carbon dioxide a pressure of 275 to 325 bar, and at a temperature of between 140° F. to 163° F. In one embodiment, the prepared broccoli seed is treated at 300 bar and a temperature of 145° F. At this temperature, myrosinase is not deactivated, while ESP is deactivated and pathogens are killed. The prepared broccoli seed may be treated in a batch process or a continuous process. The time for the treatment may be adjusted to achieve the desired degree of deoiling. In one embodiment, the prepared seed is treated in a batch process for a period of 2-3 hours. The resulting broccoli seed product contains active myrosinase and deactivated ESP. This process results in a seed meal that contains 20-30% of the original volume of oil. This natural broccoli seed oil has been shown in stability testing to preserve the viability of the myrosinase enzyme.

The deoiled prepared broccoli seed may be combined with the glucoraphanin rich meal prepared as described above to produce a nutritional supplement that will provide a source of sulforaphane in the intestine when ingested. The proportion of each component may be adjusted depending upon the levels of glucoraphanin in the meal and myrosinase in the deoiled seed. Typically, the proportion of deoiled prepared broccoli seed to glucoraphanin rich meal will be in the range of 1:3 to 1:1. The invention is not limited in this regard, and any desired proportion of the first and second broccoli materials may be used in the nutritional supplement.

The nutritional supplement may be sized to provide the desired amount of sulforaphane when ingested. For example, the total weight of active ingredients may range from 100 mg to 1000 mg or more. In one embodiment, the nutritional supplement comprises about 150 mg of deoiled prepared broccoli seed and about 325 mg of glucoraphanin rich meal.

The nutritional supplement may also contain an ascorbate, such as calcium ascorbate. Calcium ascorbate is known to increase the activity of myrosinase. Calcium ascorbate is provided in small amounts relative to the other components of the supplement typically 0.1 mg or less. In the embodiment described above, the calcium ascorbate is present in an amount of about 0.004 mg.

The nutritional supplement may be provided a capsule. The capsule may be acid resistant or have an enteric coating to avoid having the contents of the capsule released in the stomach and degraded.

EXAMPLE 1

A first quantity of broccoli seed meal was produced by the following process. Approximately 1 kg of broccoli seed was prepared for treatment by flaking and rolling. The broccoli seed contains approximately 40% by weight oil. A counter rotating flake roller was set at 0.005 gap, and the raw seed was fed slowly by gravity. The result was the formation of a "potato chip" type of appearance. The prepared broccoli seed was placed in a SCFE chamber and treated at about 600 bar and about 185° F. for 1.5-2 hours hours using $CO_2$ as the solvent. The resulting seed meal contained approximately 1-3% oil by weight in the finished product. The resulting product is a glucoraphanin rich meal with the myrosinase and the ESP in the meal both deactivated.

EXAMPLE 2

A second quantity of broccoli seed meal was produced by the following process. Approximately 1 kg of broccoli seed containing approximately 40% by weight oil was prepared for treatment by flaking and rolling. A counter rotating flake roller was set at 0.005 gap, and the raw seed was fed slowly by gravity. The result was the formation of a "potato chip" type of appearance. The prepared broccoli seed was placed in a SCFE chamber and treated at about 300 bar and about 140° F. for 3-3.5 hours using CO2 as the solvent. The resulting seed meal contained approximately 8-10% oil by weight in the finished. The resulting product contains active, stable myrosinase with the ESP deactivated.

EXAMPLE 3

A nutritional supplement was prepared by combining 325 mg of the glucoraphanin rich meal of Example 1 with 125 mg of the product of Example 2, and 0.004 mg of calcium ascorbate. An acid resistant capsule was filled with the materials to produce the nutritional supplement.

The nutritional supplement of Example 3 was tested in vitro to determine the amount of sulforaphane released from the supplement when dissolved in water. Approximately 0.65 moles of sulforaphane were released for every mole of glucoraphanin in the supplement. This compares to a release 0.15 moles of sulforaphane per mole of glucoraphanin from natural, untreated broccoli. The nutritional supplement of Example 3 can release up to about 8 mg of sulforaphane in the intestine.

One advantage of the present invention is that an all natural or organic nutritional supplement can be provided that can release sulforaphane in the intestines. Another advantage of the present invention is that by using the deoiled broccoli products, micronutrients in the broccoli material in addition to the sulforaphane are available in the nutritional supplement. Other advantages of the invention will be apparent to those skilled in the art.

As will be recognized by those of ordinary skill in the art based upon the teaching herein, numerous changes and modifications may be made to the above-described and other embodiments of the invention without departing from its scope as defined in the appended claims. For example, the relative quantities of the ingredients may be varied or additional ingredients may be added to the nutritional supplement. Accordingly, the description of preferred embodiments provided above is to be taken in an illustrative rather than a limiting sense.

What is claimed is:

1. A process for producing a broccoli supplement containing active myrosinase enzyme comprising the steps of:
   (a) providing a first and second broccoli product comprising broccoli seeds or sprouts;
   (b) preparing the first and second broccoli products for treatment to remove oils contained in the broccoli products;
   (c) treating the first prepared broccoli product using supercritical fluid extraction with carbon dioxide at a temperature of about 185° F. or greater and a pressure of up to about 600 bar;
   (d) treating the second prepared broccoli product using supercritical fluid extraction with carbon dioxide at a temperature of between about 140° F. to about 175° F. to remove oils contained in the broccoli product and to deactivate ESP contained in the broccoli product, wherein the resulting broccoli product comprises active myrosinase enzyme; and
   (e) combining the first and second treated broccoli products.

2. The process of claim 1, wherein the first and second broccoli products are broccoli seeds.

3. The process of claim 1, wherein the first and second broccoli products are prepared for treatment by one of grinding, chopping, milling or rolling.

4. The process of claim 2, wherein the first and second quantities of broccoli seeds are prepared for treatment by rolling and flaking to produce a broccoli seed meal.

5. The process of claim 1, wherein the second prepared broccoli product is treated using supercritical carbon dioxide at a pressure of between about 275 to about 325 bar and at a temperature of between about 140° F. to 175° F.

6. The process of claim 4, wherein the second prepared broccoli seeds are treated using supercritical carbon dioxide at a pressure of about 300 bar and at a temperature of about 145° F.

7. A nutritional supplement comprising:
(a) a first deoiled broccoli seed meal, wherein the broccoli seed meal comprises less than 2% by weight oil and wherein substantially all of the myrosinase and ESP in the broccoli seed meal is deactivated;
(b) a second deoiled broccoli seed meal containing active myrosinase and deactivated ESP:
(c) an ascorbate and
(d) an acid resistant capsule.

* * * * *